United States Patent [19]

Driscoll et al.

[11] 4,105,774

[45] Aug. 8, 1978

[54] HYDANTOIN COMPOUNDS AND METHODS OF USE THEREOF

[75] Inventors: John S. Driscoll, Rockville, Md.; Victor E. Marquez, Caracas, Venezuela; Geoffrey Peng, Chicago, Ill.

[73] Assignee: The United States of America as represented by the Secretary of State, Washington, D.C.

[21] Appl. No.: 599,602

[22] Filed: Jul. 28, 1975

[51] Int. Cl.² .................. H61K 31/415; C07D 233/20
[52] U.S. Cl. .................................. 424/273 R; 548/312
[58] Field of Search .................... 260/309.5; 424/273; 548/312

[56] References Cited

PUBLICATIONS

Chemical Abstracts 83:157713w (1975).

*Primary Examiner*—Jerome D. Goldberg
*Attorney, Agent, or Firm*—Holman & Stern

[57] ABSTRACT

Hydantoin derivatives of varying lipophilic character were prepared as nitrogen mustard carriers for CNS anti-tumor evaluation in transplanted mouse tumor test systems. Activity was studied in the murine ependymoblastoma brain tumor system. Multiple cures were observed for three of the four analogs examined. The compounds were also active in the intraperitoneal leukemia L1210 and P388 systems as well as in B16 melanoma and Lewis lung carcinoma.

3 Claims, 15 Drawing Figures

HYDANTOIN COMPOUNDS AND METHODS OF USE THEREOF

BACKGROUND OF THE INVENTION

This invention relates to hydantoin compounds and methods of use thereof, and more particularly this invention relates to novel hydantoin compounds which have anti-tumor activity against transplanted mouse tumor test systems.

The design of drugs which have potential utility in the chemotherapy of tumors of the central nervous system contains numerous challenges. In addition to possessing antitumor activity, a potential anti-tumor agent should have structural features which allow it to circumvent natural defense mechanisms, such as the blood-brain-barrier (BBB). There appear to be significant differences in the anatomical structure of brain tumors and their surrounding areas compared to normal brain. While the neoplasm appears to alter the BBB in such a way that drug penetration is sometimes enhanced, the changes are not constant among different types of brain tumors. This indicates that the permeability properties are not altered to the same extent and the BBB is a factor which must be considered. The situation is complex and in seeking new anti-tumor drugs, one should be concerned with the type of structure which (a) penetrates the BBB (b) does so in significant concentrations and (c) has anti-tumor activity.

The principle of using a carrier for an anti-tumor active functional group, e.g. a nitrogen mustard, is not new, and phenylalanine mustard (sarcolysin) is an example of this application. In a recent review of CNS antitumor agents, Broder and Rall concluded that new drug emphasis should be placed on alkylating agents which are able to cross the BBB. The reports that 5,5-diphenylhydantoin penetrated the BBB in significant concentrations and localized in brain tumors relative to surrounding normal brain tissue but had no anti-tumor activity, prompted a study of hydantoins as carriers for nitrogen mustard groups in an attempt to prepare agents which might have utility as drugs for CNS and brain tumors. Mauger and Ross have previously used the hydantoin ring as a carrier in a series of active bis-2-chloroethylaminoaryl hydantoins which were tested against the Walker tumor system.

SUMMARY OF THE INVENTION

The importance of the partition coefficient as a parameter in CNS drug activity has been shown and quantitated. 5,5-Diphenylhydantoin has a log P value of 2.47 in the octanol-water system. This value approximates an optimum value (log $P_o$) of about 2.0 found to be characteristic of many CNS agents. We have postulated and have found, that the addition of an alkylating group to 5,5-diphenylhydantoin to yield the 5,5-diphenylhydantoin mustard (compound 16 in Table I) should significantly alter the partition coefficient of the compound relative to DPH. An approximation of the log P of compound 16 as the neutral molecule can be made as seen in equation 1.

$$\log P \,(DPH) + \log P(Et_3N) + 2\pi(Cl) = \log P$$

$$2.47 + 1.44 + 2(0.39) = 4.69 \qquad (1)$$

This modification to DPH might, therefore, alter its log P value in such a way as to minimize its CNS properties. Because of the large increase in lipophilic character caused by the addition of the $CH_2CH_2N(CH_2CH_2Cl)_2$ group, the carrier hydantoin was modified in order to compensate. Analogous compounds having log P values in the range of about −1 to +4 are contemplated by the invention with the range of about +1 to +3 being preferred. An additional four derivatives (compounds 17–20 in Table I) were chosen for synthesis based on their estimated log P values (1.5–2.7). After compounds 16–20 were synthesized, attempts were made to measure the partition coefficients of several of these molecules by the method of Hansch [A. Leo, C. Hansch and D. Elkins, Chem. Rev. 71, 525 (1971)]. These experiments, however, were not successful because of solution decomposition problems. This is often the case with bis(2-chloroethyl) derivatives.

Thus, in its broadest terms, the instant invention, in a first aspect, is drawn to compounds of the general formula wherein $R_1$ and $R_2$ may be the same or different and are lower alkyl, lower hydroxyalkyl, —H, phenyl, or $R_1$ and $R_2$ together are —$CH_2(CH_2)_nCH_2$— where $n=2$ or 3 (that is, $R_1$ and $R_2$ together with the ring carbon to which they are attached are spirocyclopentyl or spirocyclohexyl and pharmaceutically acceptable salts thereof. By lower alkyl is meant alkyl of from 1 to 5 carbon atoms, including various isomeric forms. Typical pharmaceutically acceptable salts, which are examplary but are not, in any way, to be taken as limiting are the pharmaceutically tolerable salts of organic or inorganic acids such as hydrochloric, sulfuric, phosphoric, citric, lactic, and succinic acids. In a second aspect of the invention, compositions of these compounds in pharmaceutically acceptable carriers such as physiological saline, distilled water, and the like all well-known in the art, are contemplated. In a third aspect of the invention, the method of use of the compounds as a method of treating transplanted mouse tumors is contemplated. In a fourth aspect of the invention, various compounds having a utility as intermediates in the preparation of the first-mentioned compounds is contemplated, with certain of these compounds having other utilities. These intermediate compounds have the general formula wherein $R_1$ and $R_2$ are as earlier defined, but where $R_1$ and $R_2$ could both be phenyl; and wherein $R_3$ is —$CH_2CH_2Cl$ or —$CH_2CH_2N$—$(CH_2CH_2OH)_2$; and pharmaceutically acceptable salts thereof.

It is, therefore, a primary object of the present invention to provide novel hydantoin compounds having anti-tumor activity against transplanted mouse tumor test systems.

It is another object of the invention to provide compositions of the compounds according to the preceding object for use in treating transplanted mouse tumors.

It is another primary object of the present invention, consistent with the foregoing objects, to provide a method of treating transplanted mouse tumors.

It is yet another object of the present invention to provide certain novel hydantoin compounds which have utility as intermediates in the preparation of the compounds according to the first object.

It is still another object of the present invention to provide a novel hydantoin compound having anticonvulsent activity.

These objects as well as other objects which will become apparent as the description proceeds are implimented by the instant invention and will be more readily and comprehensively understood from the following detailed description of the preferred embodiments. Such description makes reference to the attached drawings.

DESCRIPTION OF THE PREFERRED EMBODIMENTS

The initial member of the series of compounds tested for anti-tumor properties against transplanted mouse tumor test systems, compound 16 of Table I, was prepared by two procedures. An earlier hydantoin study [V. E. Marquez, L. M. Twanmoh, H. B. Wood, Jr., and J. S. Driscoll, *J. Org. Chem.*, 37, 2558 (1972)] had produced the bicyclic compound During an investigation of the alkylating properties of this compound, it was reacted with diethanolamine to produce compound 11 of Table I which was subsequently converted to compound 16 of Table I by the following series of reactions:

A more general method employed a 3-(β-chloroethyl) hydantoin, and the other compounds of the instant invention were made by this method according to the following scheme:

| Compounds | Substituents |
|---|---|
| 1,6,11,16; | $R_1 = R_2 = C_6H_5$ |
| 2,7,12,17; | $R_1 + R_2 = (CH_2)_5$ |
| 3,8,13,18; | $R_1 = R_2 = CH_3$ |
| 4,9,14,19; | $R_1 = R_2 = C_2H_5$ |
| 5,10,15,20; | $R_1 = H; R_2 = C_6H_5$ |

As mentioned earlier, the compounds of the instant invention for use in treating transplanted mouse tumors were originally postulated as having potential as CNS anti-tumor agents due to the log P (log partition coefficient) value in the range already mentioned, with the range of +1 to +3 as being optimum. The following compounds, having the same basic structure, are also contemplated by the instant invention, these compounds being listed in terms of the $R_1$ and $R_2$ substituents on the basic structure:

| $R_1$ | $R_2$ | Calculated log P value |
|---|---|---|
| $CH_2OH$ | $CH_2OH$ | −0.79 |
| $CH_2CH_2OH$ | $CH_2CH_2OH$ | +0.21 |
| $(CH_2)_3OH$ | $(CH_2)_3OH$ | +1.21 |
| $(CH_2)_4OH$ | $(CH_2)_4OH$ | +2.21 |
| $(CH_2)_4OH$ | $(CH_2)_4OH$ | +3.21 |
| $CH_2CH_2CH_3$ | $CH_2CH_2CH_3$ | +3.53 |
| $CH_2CH_3$ | $CH_3$ | +2.03 |
| $(CH_2)_3CH_3$ | H | +2.53 |
| $CH_2CH_2CH_3$ | H | +2.03 |

It will be quite apparent to those skilled in the art that the various substituents for $R_1$ and $R_2$ may be the same or different and may be various combinations of lower alkyl groups, lower hydroxyalkyl groups, hydrogen, and phenyl, all as defined above, as long as the log P value falls within the usable range.

As already mentioned, the compounds are generally prepared by the method employing a 3-($\beta$-chloroethyl) hydantoin. Specific examples which are to be considered representative and not limiting since each of the compounds can be prepared by one skilled in the art following the reaction scheme are given below.

It is noted that melting points are uncorrected and recorded on a Thomas-Hoover capillary melting point apparatus. Elemental analyses were performed by NIAMD, NIH, Bethesda, Maryland. 5,5-Diphenylhydantoin was obtained from a commerical source. 5-Phenylhydantoin and 5,5-dimethylhydantoin were obtained commercially. Compounds 2 and 4 were prepared from the corresponding ketones by the method of Upham and Dermer (British Pat. No. 752,692 (1956) which is embodied herein by reference.) New compounds were identified by nmr and ir spectroscopy. Satisfactory elemental analyses (±0.4% of calculated values) are indicated by elemental symbols in Table II.

EXAMPLE I 5,5-Pentamethylene-3-(2'-chloroethyl)hydantoin 5,5-Pentamethylenehydantoin, 4.2 gm (0.025 mol) was dissolved in a solution of 1.5 gm (0.025 mol) of KOH in 100 ml ethanol. To this solution was added 7.2 gm (0.05 mol) of 1-bromo-2-chloroethane in one portion. The resulting solution was refluxed and stirred for 8 hours. Evaporation of the reaction mixture gave a white solid which was shaken with ethyl acetate and water in a separatory funnel. The organic layer was separated, washed (10% aqueous $NaHCO_3$), dried ($Na_2SO_4$), and evaporated to give 4.2 gm (73%) of compound 7. Recrystallization from benzene/isopropanol gave white crystals, mp 156°–158°.

EXAMPLE II 3-(2-(Bis-2'-hydroxyethyl)-amino)-ethyl)-5,5-pentamethylenehydantoin Compound 7 from Example I, 3.0 gm (0.013 mol), sodium iodide, 2.8 gm (0.019 mol), and diethanolamine, 4.0 gm (0.037 mol) were dissolved in 50 ml of freshly distilled N,N-dimethylformamide and the resulting solution was heated at 90°–100° for 12 hours. After removing DMF at reduced pressure, the residue was treated with saturated aqueous $NaHCO_3$ solution and this solution was extracted with ethyl acetate. The ethyl acetate solution was washed ($H_2O$), dried ($Na_2SO_4$), and evaporated to give an oil. Compound 12 [2.4 gm (63%)] was isolated by chromatographic purification on silica gel with acetone/benzene (1:1 v/v) as eluent. The analytical sample, mp 100°–102°, was prepared by recrystallization from benzene/isopropanol.

EXAMPLE III 3-(2-(Bis-(2'-chloroethyl)-amino)-ethyl)-5,5-pentamethylenehydantoin Compound 12 from Example II, 3.0 gm (0.01 mol), was added to 25 ml of phosphorus oxychloride. The mixture was heated at 70°–90° for 1.5 hr. Phosphorus oxychloride was removed at reduced pressure to yield an oily residue which was treated with 10 ml of concentrated hydrochloric acid. After the initial exothermic reaction subsided, the mixture was heated on a steam bath for 10min and allowed to cool. The mixture was poured into a cold saturated NaOAC solution and the solution was extracted with ethyl acetate. After washing ($H_2O$), drying ($Na_2SO_4$), and evaporation, the ethyl acetate extract yielded an oil which solidified upon cooling. Recrystallization from isopropanol gave 1.67 gm (51%) of compound 17, mp 125°–126°.

The compounds made according to this procedure are listed in Table I along with percentage yield, melting point, molecular formula, and reference to the Figures showing the nmr or ir spectra. Several of the intermediate products were oils. In those instances, yields were computed based on the first crystalline material isolated. The elemental analytical data is tabulated in Table II.

TABLE I
Physical and Chemical Data

Figure 1:
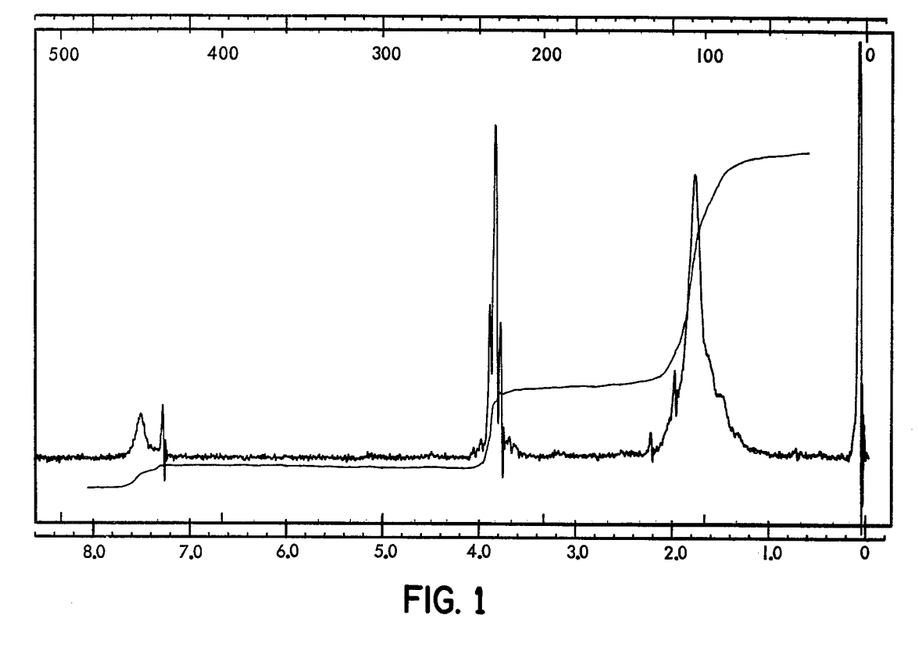
FIGS. 1 through 10 are nuclear magnetic resonance spectra of certain of the compounds of the instant invention and FIGS. 11 through 15 are infrared spectra of certain compounds of the instant invention.
Figure 2:
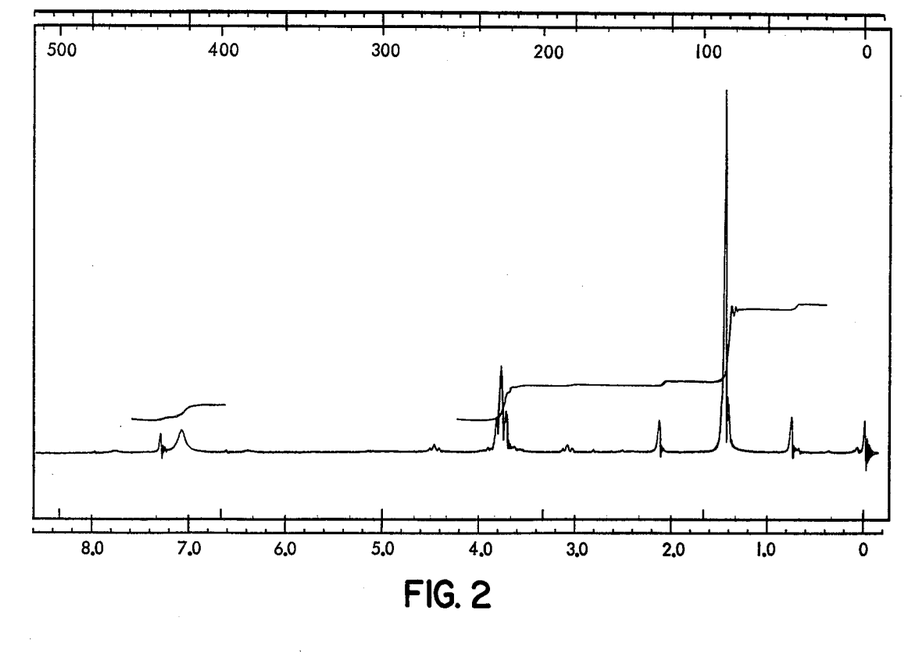
Figure 3:
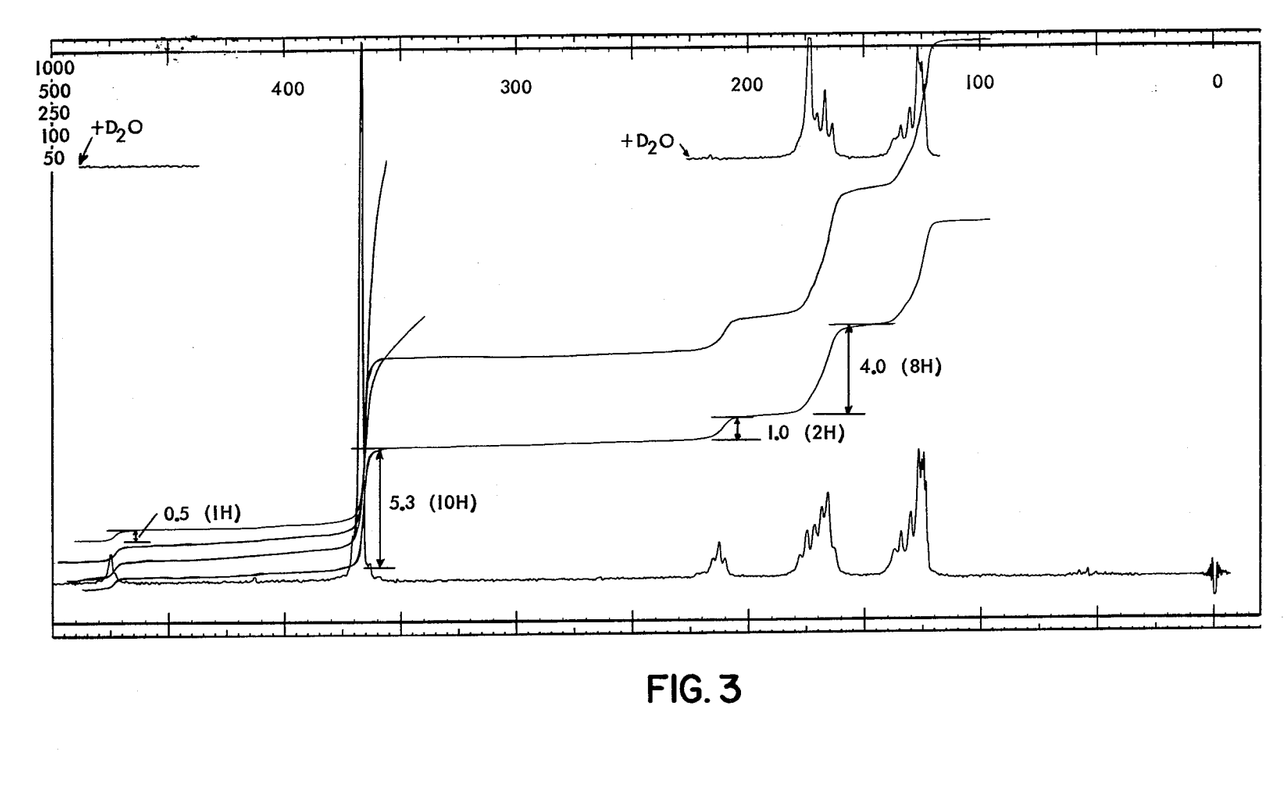
Figure 4:
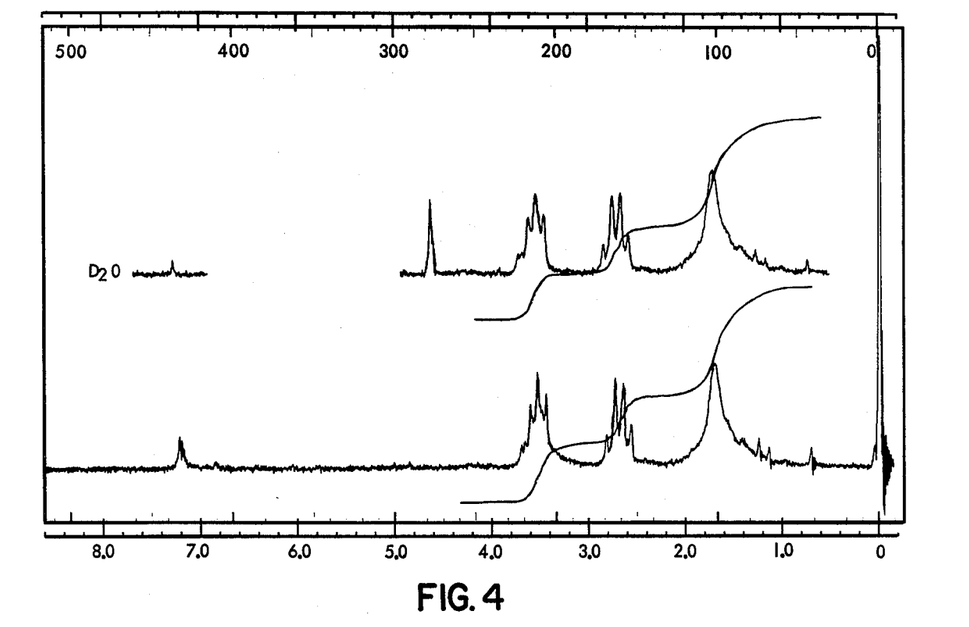
Figure 5:
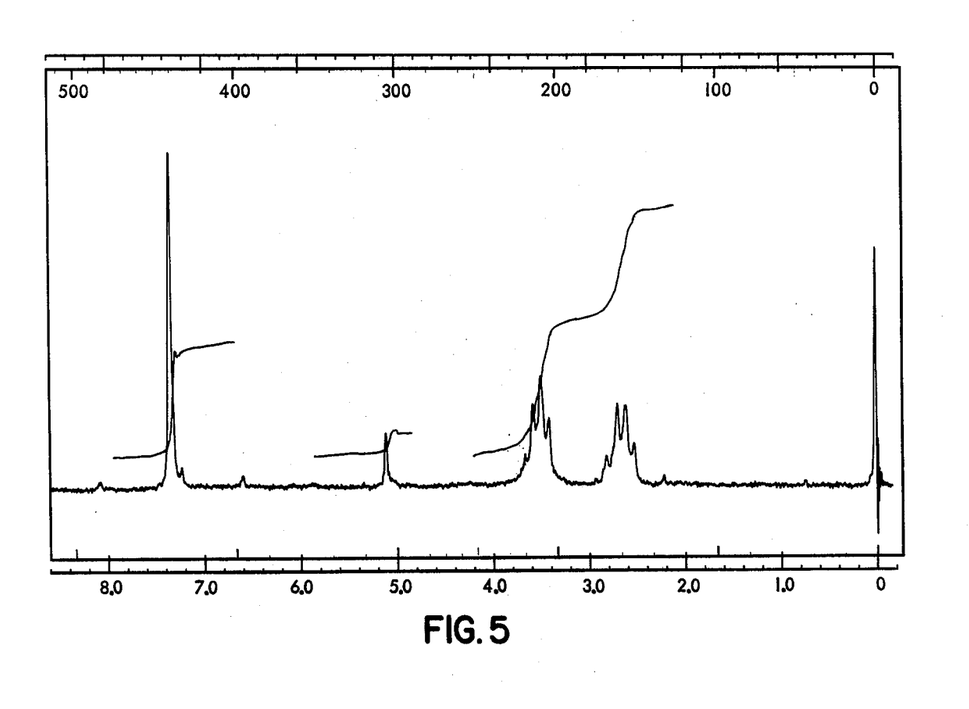
Figure 6:
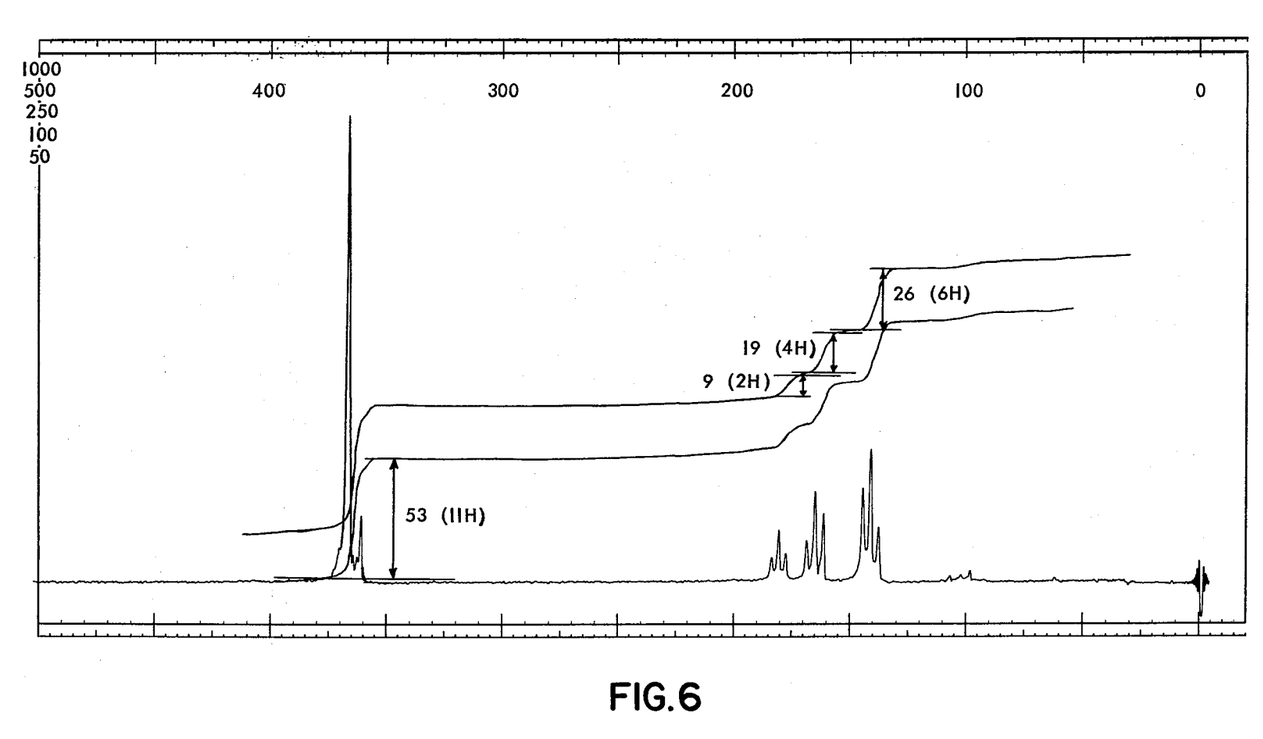
Figure 7:
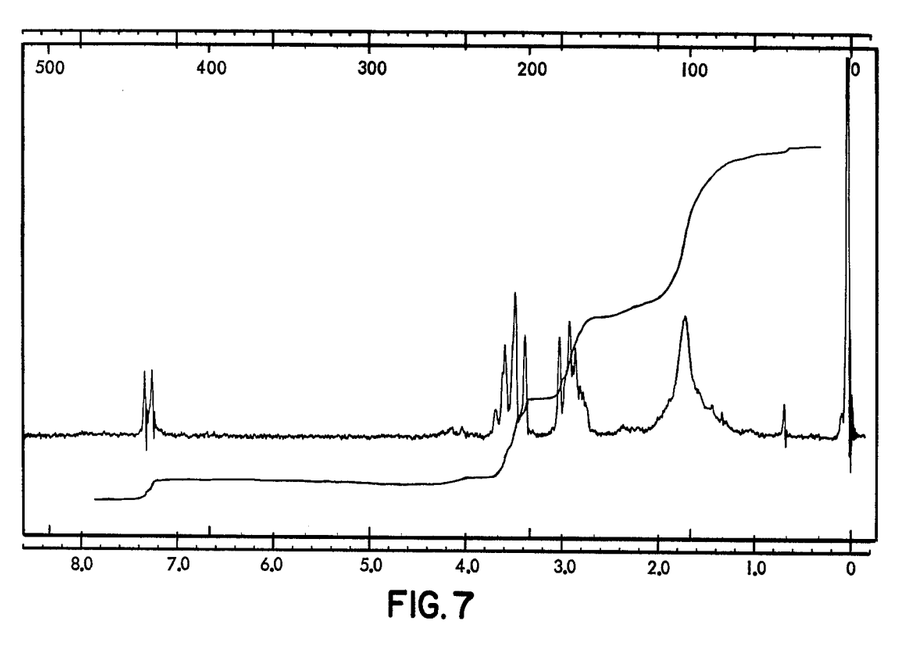
Figure 8:
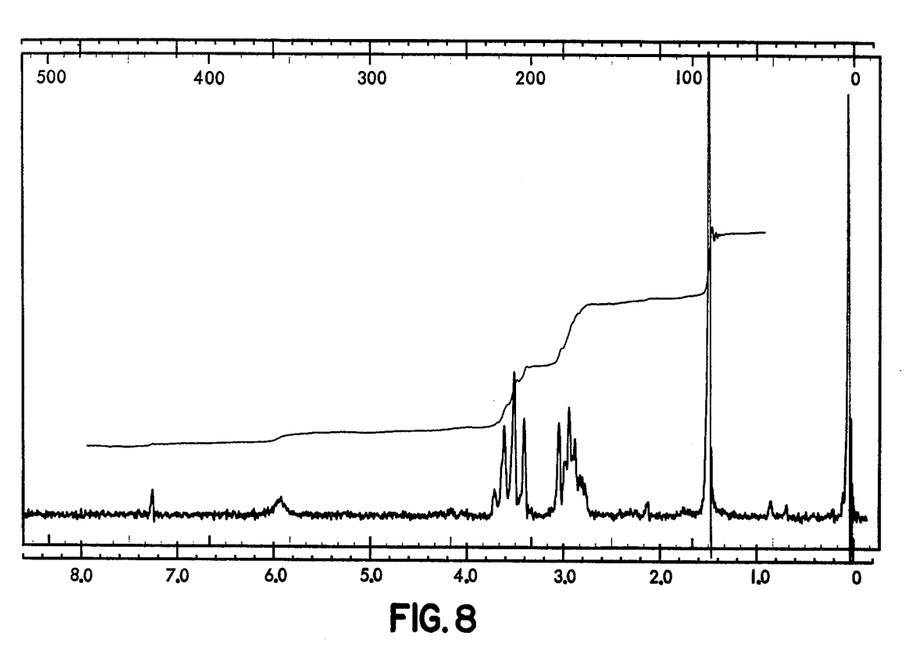
Figure 9:
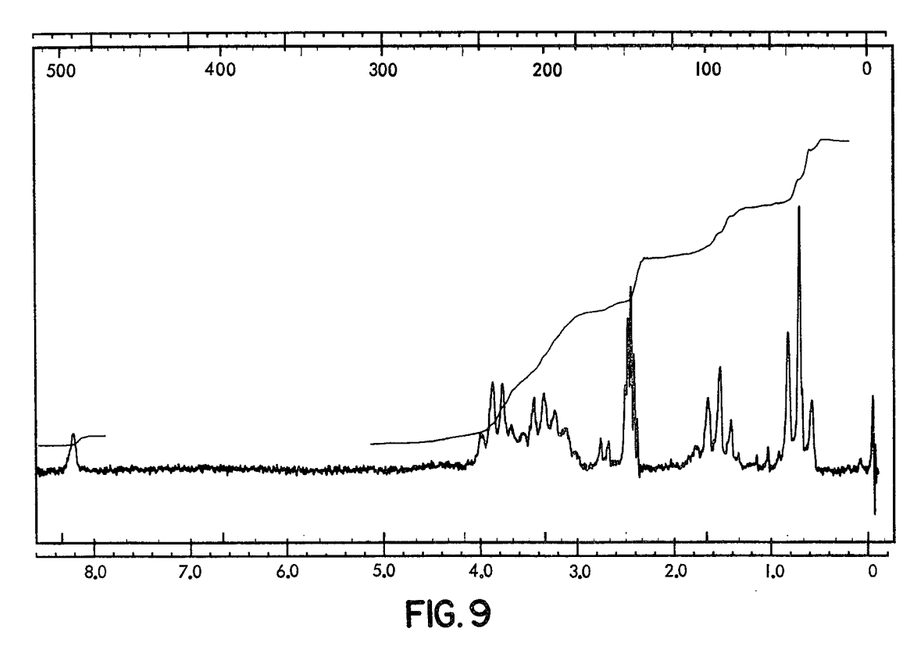
Figure 12:
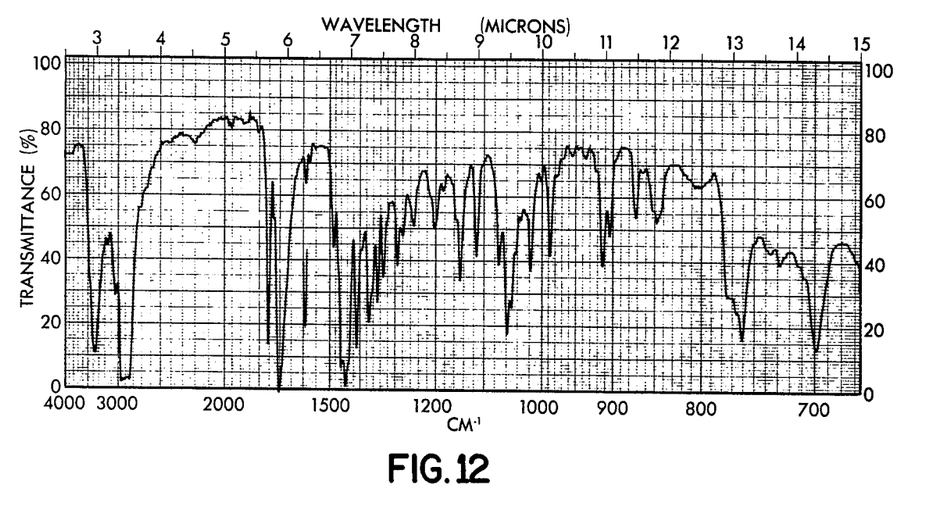
Figure 13:
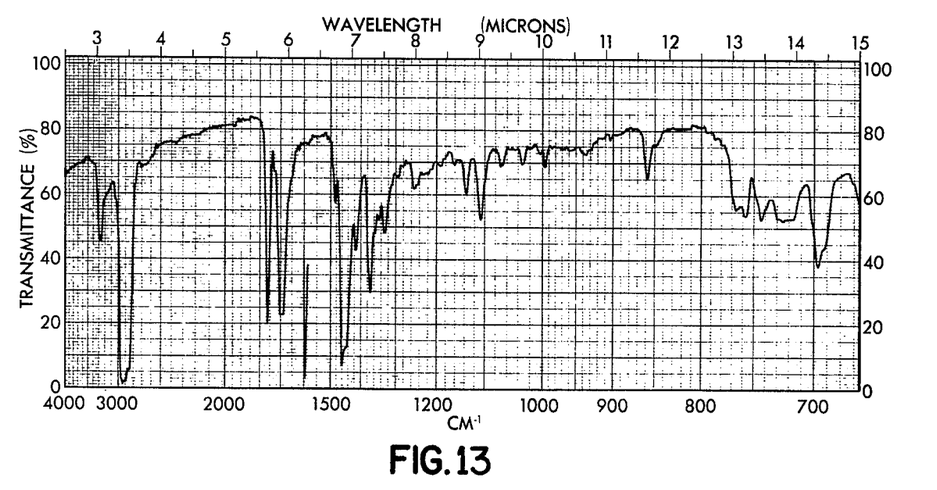
Figure 14:
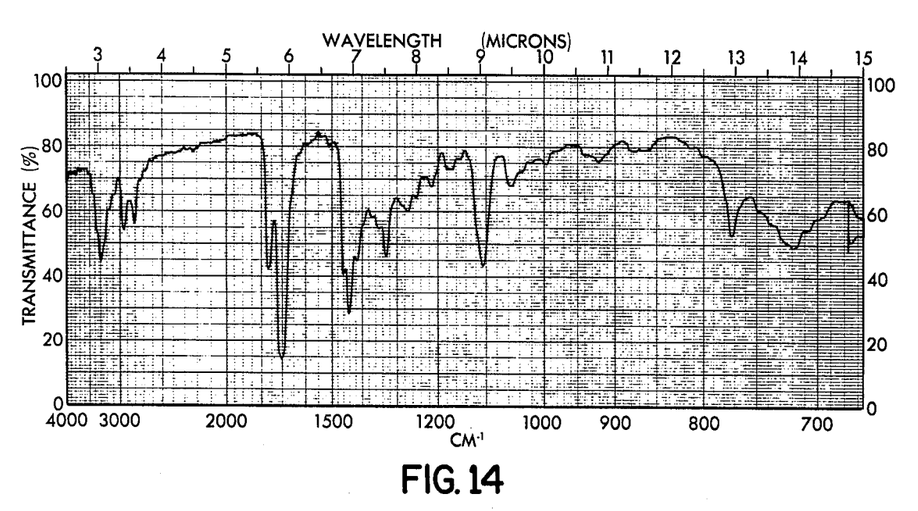

| Compound No. | $R_1$ | $R_2$ | $R_3$ | Yield % | m.p° C | Mol.Formula | Spectra |
|---|---|---|---|---|---|---|---|
| 2 | $CH_2CH_2CH_2CH_2CH_2$ | | H | 88 | 215–215.5 (a) | $C_8H_{12}N_2O_2$ | |
| 4 | $C_2H_5$ | $C_2H_5$ | H | 55 | 164–165.5 (b) | $C_7H_{12}N_2O_2$ | |
| 6 | $C_6H_5$ | $C_6H_5$ | $CH_2CH_2Cl$ | 47 | 150–152 | $C_{17}H_{15}N_2O_2Cl$ | |
| 7 | $CH_2CH_2CH_2CH_2CH_2$ | | $CH_2CH_2Cl$ | 73 | 156–158 | $C_{10}H_{15}N_2O_2Cl$ | FIG. 1 |
| 8 | $CH_3$ | $CH_3$ | $CH_2CH_2Cl$ | 77 | 94.5–96 | $C_7H_{11}N_2O_2Cl$ | FIG. 2 |
| 11 | $C_6H_5$ | $C_6H_5$ | $CH_2CH_2N(CH_2CH_2OH)_2$ | 87 | 145 | $C_{21}H_{25}N_3O_4$ | FIGS. 3 & 12 |
| 12 | $CH_2CH_2CH_2CH_2CH_2$ | | $CH_2CH_2N(CH_2CH_2OH)_2$ | 63 | 100–102 | $C_{14}H_{25}N_3O_4$ | FIG. |
| 15 | H | $C_6H_5$ | $CH_2CH_2N(CH_2CH_2OH)_2$ | 28 (C) | 108–110 | $C_{15}H_{21}N_3O_4$ | FIG. 5 |
| 16 | $C_6H_5$ | $C_6H_5$ | $CH_2CH_2N(CH_2CH_2Cl)_2$ | 68 | 146–147.5 | $C_{21}H_{23}N_3O_2Cl_2$ | FIGS. 6 & 13 |
| 17 | $CH_2CH_2CH_2CH_2CH_2$ | | $CH_2CH_2N(CH_2CH_2Cl)_2$ | 51 | 125–126 | $C_{14}H_{23}N_3O_2Cl_2$ | FIG.7 |
| 18 | $CH_3$ | $CH_3$ | $CH_2CH_2N(CH_2CH_2Cl)_2$ | 24 (d) | 70–72 | $C_{11}H_{19}N_3O_2Cl_2$ | FIGS. 8 & 14 |
| 19 | $C_2H_5$ | $C_2H_5$ | $CH_2CH_2N(CH_2CH_2Cl)_2$ | 18 (e) | 157–158 | $C_{13}H_{24}N_3O_2Cl_3$ (f) | FIG.9 |
| 20 | H | $C_6H_5$ | $CH_2CH_2N(CH_2CH_2Cl)_2$ | 41 | 74–75 | $C_{15}H_{19}N_3O_2Cl_2$ | FIGS. |

TABLE I-continued

Physical and Chemical Data

Figure 10:
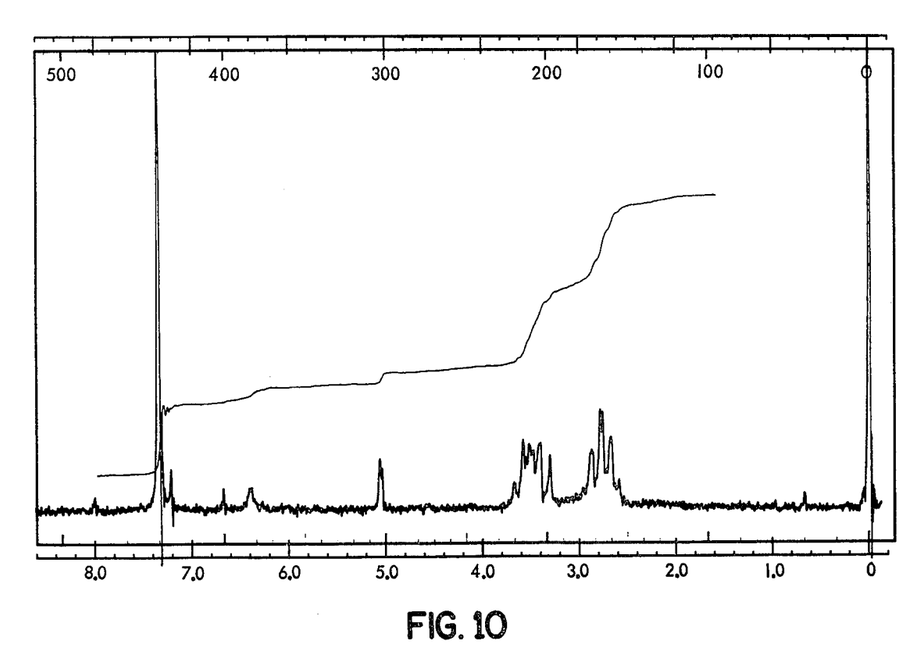
Figure 11:
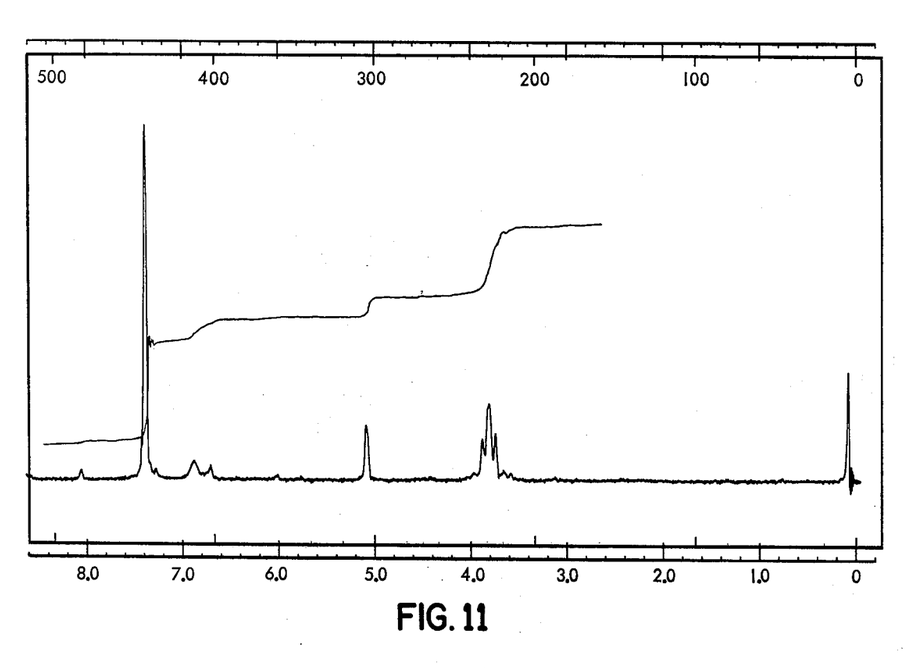
Figure 15:
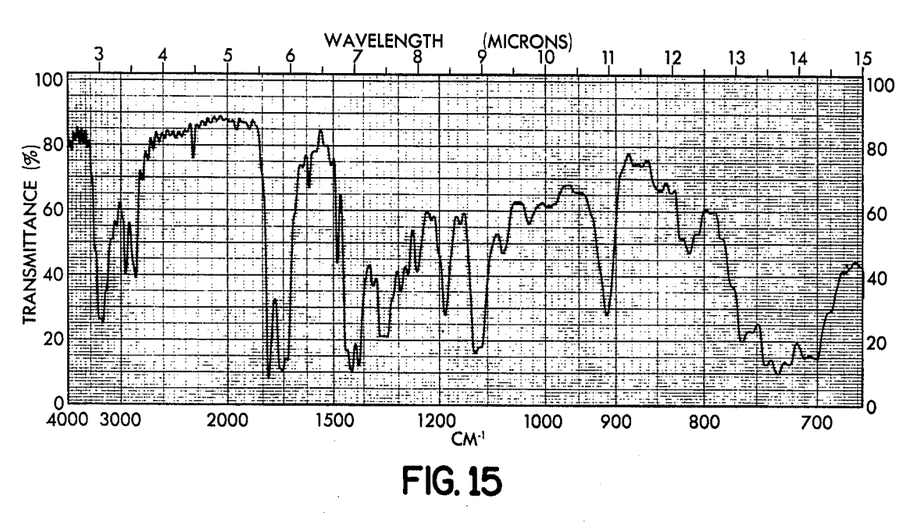

| Compound No. | $R_1$ | $R_2$ | $R_3$ | Yield % | m.p° C | Mol.Formula | Spectra |
|---|---|---|---|---|---|---|---|
| | | | | | | | 10 & 15 |

(a) lit. mp 215–215.5°
(b) lit. mp 165°
(c) from 5-phenylhydatoin (compound 5)
(d) from 5,5-dimethyl-3-(2-chloroethyl) hydantoin (compound 8)
(e) from 5,5-diethyl hydantoin (compound 4)
(f) HCl salt

TABLE II

ELEMENTAL ANALYTICAL DATA

| | | | | FOUND | | | CALCULATED | | |
|---|---|---|---|---|---|---|---|---|---|
| Compd. | $R_1$ | $R_2$ | $R_3$ | C | H | N | C | H | N |
| 2 | $CH_3CH_2CH_2CH_2CH_2$ | | H | 56.90 | 7.19 | 16.64 | 57.14 | 7.14 | 16.67 |
| 4 | $C_2H_5$ | $C_2H_5$ | H | 54.17 | 8.01 | 17.78 | 53.85 | 7.69 | 17.95 |
| 6 | $C_6H_5$ | $C_6H_5$ | $CH_2CH_2Cl$ | 64.77 | 4.85 | 8.91 | 64.86 | 4.80 | 8.90 |
| 7 | $CH_3CH_2CH_2CH_2CH_2$ | | $CH_2CH_2Cl$ | 51.78 | 6.56 | 11.91 | 52.06 | 6.51 | 12.15 |
| 8 | $CH_3$ | $CH_3$ | $CH_2CH_2Cl$ | 43.87 | 5.54 | 14.53 | 44.09 | 5.77 | 14.70 |
| 11 | $C_6H_5$ | $C_6H_5$ | $CH_2CH_2N(CH_2CH_2OH)_2$ | 65.45 | 6.79 | 10.78 | 65.77 | 6.57 | 10.96 |
| 12 | $CH_3CH_2CH_2CH_2CH_2$ | | $CH_2CH_2N(CH_2CH_2OH)_2$ | 56.35 | 8.34 | 14.14 | 46.19 | 8.36 | 14.05 |
| 16 | $C_6H_5$ | $C_6H_5$ | $CH_2CH_2N(CH_2CH_2Cl)_2$ | 60.02 | 5.48 | 10.00 | 60.10 | 5.62 | 9.91 |
| 17 | $CH_3CH_2CH_2CH_2CH_2$ | | $CH_2CH_2N(CH_2CH_2Cl)_2$ | 50.04 | 6.94 | 12.45 | 50.01 | 6.89 | 12.49 |
| 18 | $CH_3$ | $CH_3$ | $CH_2CH_2N(CH_2CH_2Cl)_2$ | 44.30 | 6.35 | 13.98 | 44.00 | 6.33 | 14.00 |
| 19 | $C_2H_5$ | $C_2H_5$ | $CH_2CH_2N(CH_2CH_2Cl)_2$ · HCl | 43.50 | 6.90 | 11.57 | 43.27 | 6.66 | 11.65 |
| 20 | H | $C_6H_5$ | $CH_2CH_2N(CH_2CH_2Cl)_2$ | 52.20 | 5.52 | 11.98 | 52.34 | 5.56 | 12.21 |
| 15 | H | $C_6H_5$ | $CH_2CH_2N(CH_2CH_2OH)_2$ | 58.46 | 6.75 | 13.40 | 58.63 | 6.84 | 13.86 |

Antitumor Activity Against Transplanted Mouse Tumor Test Systems

All compounds described (1–21) were tested in the lymphoid leukemia L1210 system by standard NCI protocols (R. I. Geran et al., Cancer Chemo. Reports, Part 3, 3, No. 2, 1 (1972) which is embodied herein by reference in its entirety). Only compounds 16–20 showed enough activity to be further tested in additional transplanted mouse tumor test systems. In addition to leukemia L1210, these compounds were tested against lymphocytic leukemia P388, B16 melanocarcinoma, Lewis lung carcinoma and the ependymoblastoma mouse brain tumor. All T/C results reported in Table III have been reproduced in separate experiments to give values not more than 15% lower than the value in the Table.

to or greater than the following: L1210 leukemia, 125%; P388 leukemia, 125%; B16 melanoma, 140%; Lewis lung carcinoma, 125%; Ependymoblastoma, 140%]. L1210 activity would have to be considered only moderate for compounds 17–19. It can be noted that there is a significant difference between the optimal doses of the diphenyl analog (compound 16) and the other derivatives. Compounds 17, 18 and 19 exhibited no intracerebral L1210 activity. This might be expected, however, based on the marginal L1210 intraperitoneal activity.

Substantial activity is noted in the leukemia P388 tests with the pentamethylene (compound 17) and diethyl (compound 19) derivatives having the greatest activity. Multiple cures (30 day survivors) were observed with both compounds.

Compounds 16, 17 and 19 had approximately the same level of activity in the B16 melanocarcinoma

TABLE III

| | Antitumor Activity[a] | | | | | | | | | |
|---|---|---|---|---|---|---|---|---|---|---|
| | L1210 Lymphoid Leukemia[b] | | P388 Lymphocytic Leukemia[c] | | B16 Melano-carbinoma[c,d] | | Lewis Lung carcinoma[c,e] | | Ependymo-biastoma[f] | |
| Compound | OD[g] | T/C[h] | OD | T/C | OD | T/C | OD | T/C | OD | T/C |
| 16 | 100 | 121 | 50 | 200[b] | 6 | 161 | — | — | 50 | 117 |
| 17 | 35 | 137 | 12.5 | 324 | 6 | 161 | — | — | 12.5 | 271 |
| 18 | 6 | 138 | 3 | 243 | 2 | 138 | 3 | 157 | 3 | 227 |
| 19 | 25 | 141 | 6 | 292 | 6 | 183 | 3 | 162 | 3 | 267 |
| 20 | 25 | 115 | 12.5 | 250 | — | — | — | — | — | — |

[a]In a minimum of one additinal experiment, these compounds were determined to have a T/C value not more than 15% lower than the value shown in this table. All compounds with active T/C values (see text for definition of activity) are confirmed active (at least one additinal active test).
[b]Day 1, 5, 9 treatment schedule.
[c]QD1-9 treatment schedule unless noted otherwise.
[d]Intraperitoneal tumor implantation.
[e]Subcutaneous tumor implantation.
[f]QD1-5 treatment schedule.
[g]Optimum dose (mg/kg/dose).
[h]T/C = (treated survival ÷ control survival × 100%.

Compounds 16–20 show substantial, reproducible activity in most of the test systems employed (Table III). Among these compounds, the 5-phenyl derivatives (compounds 16 and 20) were inactive in the L1210 system [Compounds described here are considered active if they give reproducible T/C activity values equal tumor model. Compound 18 almost reached the level of reproducible activity.

Limited testing in a second solid tumor model, Lewis lung carcinoma, showed that compounds 18 and 19 were active.

The ependymoblastoma intracerebral tumor system was used as the main test system for CNS antitumor activity. The advantages of this solid fragment implant system have been discussed (W. R. Shapiro et al., in "The Chemotherapy of Brain Tumors: A Clinical and Experimental Review", Recent Advan. Neurol., 6, 150 (1969) and R. I. Geran et al., Cancer Chemother. Repts., Part 2, 4, 53 (1974), pertinent portions of which are embodied herein by reference). The tumor is implanted in the mouse's brain and the drug is administered intraperitoneally. Following this procedure, the DPH mustard analog, Compound 16, was inactive in this test system. Compounds 17, 18 and 19, however, have very good activities. Cures (60 day survivors) of at least 50 percent were obtained with each of these compounds. In two separate tests of the spiropentamethylene derivative, (compound 17) 6 of 6 and 5 of 6 ependymoblastoma cures were obtained at the optimum dose (12.5 mg/kg).

At four times the optimum dose, the compounds in Table III were almost always toxic. A therapeutic index (TI) (highest active dose divided by lowest active dose) of at least two or four was generally encountered. In the very active tests, e.g. compounds 17, 18 and 19 in the P388 and ependymoblastoma systems, TI values of compounds 16, to 32 were not unusual.

Several derivatives (compounds 17, 18 and 19) are active in most of the tumor systems studied. The diphenyl analog, compound 16, the most lipophilic of the group, was active in two of the intraperitoneal tumor systems but inactive in the brain tumor model. With the few compounds evaluated, it is impossible to make a final conclusion concerning the relative importance of the physical parameters involved. The inactivity of the 5-phenyl derivatives in the L1210 and ependymoblastoma systems might be due to high lipophilicity, the steric effects of the groups in the 5-position or metabolic differences between aromatic and aliphatic substituted compounds. The high activity of the more moderately lipophilic derivatives in the brain tumor system is, however, consistent with the previously noted importance of drug transport properties in CNS systems.

It should now be apparent that the objects initially set forth have been successfully achieved. Moreover, while there is shown and described present preferred embodiments of the invention, it is to be distinctly understood that the invention is not limited thereto, but may be otherwise variously embodied and practiced within the scope of the following claims.

Accordingly, what is claimed is:

1. A compound selected from the group consisting of wherein $R_1$ and $R_2$ together are $-CH_2CH_2CH_2CH_2CH_2-$, and pharmaceutically acceptable salts thereof.

2. A composition for treating transplanted mouse tumors consisting essentially of an effective amount of a compound as defined in claim 1 and a pharmaceutically acceptable carrier.

3. A method of treating transplanted tumors in mice comprising administering to a tumor-bearing mouse an effective dose of the composition of claim 2.

* * * * *